United States Patent [19]
Lee et al.

[11] Patent Number: 5,856,119
[45] Date of Patent: *Jan. 5, 1999

[54] METHOD FOR MONITORING AND CONTROLLING BIOLOGICAL ACTIVITY IN FLUIDS

[75] Inventors: Jaw Fang Lee, Berwyn; Xin Yang, Holland; Sergey K. Maneshin, Upper Holland; Terrance J. Mah, Blue Bell, all of Pa.

[73] Assignee: BioChem Technology, Inc., King of Prussia, Pa.

[ * ] Notice: The term of this patent shall not extend beyond the expiration date of Pat. No. 5,698,412.

[21] Appl. No.: 589,346

[22] Filed: Jan. 22, 1996

[51] Int. Cl.$^6$ .............................. C12Q 1/04; C12Q 1/02; G01N 33/18; G01N 7/00
[52] U.S. Cl. .................................. 435/34; 435/29; 435/4; 436/62; 73/19.01; 73/19.04; 205/742
[58] Field of Search .................................. 435/34, 29, 4; 73/19, 19.01, 19.04; 210/605; 436/62; 205/742

[56] References Cited

U.S. PATENT DOCUMENTS

| | | | |
|---|---|---|---|
| 3,348,409 | 10/1967 | Arthur | 73/19 |
| 4,220,715 | 9/1980 | Ahnell | 435/34 |
| 4,537,682 | 8/1985 | Wong-Chong | 435/29 |
| 5,013,442 | 5/1991 | Davis et al. | 210/614 |
| 5,389,524 | 2/1995 | Larson et al. | 435/29 |
| 5,401,412 | 3/1995 | Yang et al. | 210/605 |

OTHER PUBLICATIONS

Wat. Sci. Tech. vol. 25, No. 6, pp. 43–57, 1992 *Characterization of Functional Microorganism Groups and Substrate in Activated Sludge and Wastewater by Aur, Nur and Our* G. Holm Kristensen, P. Elberg Jørgensen and M. Henze.
Research Journal WPCF, vol. 63, No. 3 *Effects of Oxygen Transport Limitation on Nitrification in the Activated Sludge Process* Michael K. Stenstrom, Stephen S. Song.
Operations Forum, Feb. 1994 *Alkalinity Tells All Real–Time Control For The Entire Process* A.J. Freed, K.F. Davis.
Dougherty et al., "Anaerobic Subsurface soil Microcosims: Methods to Monitor Effects of Organic Pollutants on Indigenous Microbial Activity", Toxicity Assessment: An International Journal 1989, 4, 85–104, Feb. 1, 1989.
Cao et al., "Aerobic Biodegradation and Microbial Population of a Synthetic Wastewater in a Channel with Suspended and Attached Biomass," Wat. Sci. Tech. 1995, 181–189.

*Primary Examiner*—Louise N. Leary
*Attorney, Agent, or Firm*—Miller & Christenbury

[57] ABSTRACT

A method of monitoring a microbiological process in a fluid supply involving isolation of a fluid sample from a fluid supply, measuring the pH of the fluid sample at selected time intervals, then calculating changes in pH, if any, to determine a pH variation rate for the sample. The dissolved oxygen in the sample is also measured at selected time intervals substantially synchronously with the pH measurements, and changes in dissolved oxygen, if any, are calculated to determine a biological oxygen consumption rate for the sample.

20 Claims, 10 Drawing Sheets

METHOD FOR MONITORING AND CONTROLLING BIOLOGICAL ACTIVITY IN FLUIDS

FIELD OF THE INVENTION

The present invention relates to a method for monitoring and controlling microbiological processes. More particularly, the invention relates to a method for monitoring metabolically significant transition points during the microbial metabolism of organic and inorganic substrates and controlling the microbiological process.

BACKGROUND OF THE INVENTION

Microbial use of organic and inorganic substrates in metabolic processes can cause detectable changes in measurable parameters such as pH and oxygen utilization rates. The metabolism of certain organic and inorganic nutrients results in the production of various products including, but not limited to, energy, water ($H_2O$), carbon dioxide ($CO_2$), hydroxyl ions ($OH^-$), hydrogen ions ($H^+$), and the like. As the environmental supply of exogenous organic and inorganic substrates changes, overall metabolic rates and/or patterns can change in response. Such changes can affect other measurable parameters whose values are influenced and dependent upon the presence of and/or rate at which the substrates are metabolized. The microbially mediated reactions presented below illustrate examples of how the metabolism of organic and inorganic substrates can affect measurable, dependent parameters like oxygen utilization and extracellular pH:

$$CH_3COOH + 2O_2 \rightarrow 2CO_2 + 2H_2O \quad (1)$$

$$NH_4^+ + 2O_2 \rightarrow NO_3^- + 2H^+ + H_2O \quad (2)$$

Reaction (1) describes the aerobic degradation of an organic carbonaceous substrate ($CH_3COOH$) and illustrates the direct quantitative relationship between substrate consumption and oxygen utilization. Reaction (2) describes the biologically mediated conversion of ammonia ($NH_4^+$), an inorganic substrate, to nitrate ($NO_3^-$) in a process commonly referred to as "nitrification". This reaction illustrates the direct quantitative relationship between ammonia conversion and both oxygen utilization and the production of hydrogen ions ($H^+$). The production of these hydrogen ions ($H^+$) can ultimately affect the pH of the extracellular media.

Furthermore, when $CO_2$ gas from aerobic degradation of organic substrate(s) is dissolved in water, carbonic acid, a relatively weak acid, is formed according to Reaction (3):

$$CO_2 + H_2O \leftrightharpoons H_2CO_3 \quad (3)$$

Carbonic acid dissociates in water to form carbonic and bicarbonic ions according to Reactions (4) and (5):

$$H_2CO_3 \leftrightharpoons HCO_3^- + H^+ \quad (4)$$

$$HCO_3^- \leftrightharpoons H^+ + CO_3^- \quad (5)$$

This carbonic acid "system" provides a buffering effect on the pH of the extracellular media.

Because of the quantitative nature of these biochemical reactions, the abundance and/or availability of reactants, i.e., available exogenous inorganic and organic substrates, can affect the magnitude of changes in other parameters. For example, if the nitrification reaction (2) described above is a predominant reaction within a microbial culture, the production of hydrogen ions ($H^+$) from the nitrification process would be expected to decrease markedly upon the exhaustion of readily usable ammonia ($NH_4^+$) below some metabolically critical level. Consequently, the activity of hydrogen ions in solution, i.e., pH, would also be expected to change.

Similarly, the oxygen utilization of a microbial culture would be expected to be higher in a condition in which exogenous organic substrates were readily available and plentiful than in a condition where these substrates were depleted below some metabolically significant level. In both of these examples, the measurable rate of change in pH, sometimes hereinafter referred to as "pH variation rate" or "pHPR," and oxygen utilization, sometimes hereinafter referred to as "biological oxygen consumption rate" or "BOCR," would be directly affected by the rate of substrate metabolism over time. Thus, assuming that changes in pH and oxygen consumption in a medium result from microbial metabolic activity alone, pHPR and BOCR could theoretically be used to signal metabolically significant transition points in a microbiological process.

U.S. Pat. No. 5,013,442 to Davis et al discloses a method of aerobic wastewater treatment which utilizes alkalinity as a control parameter. However, "alkalinity" is defined in Davis et al as the ability to buffer acids determined by titrating with sulfuric acid to a select end point of 4.5 pH. Thus, alkalinity as defined in Davis et al is clearly different from pH. Further, Davis et al fails to disclose the use of pHPR and/or BOCR together as control parameters for a microbiological process and also fails to teach any means for blocking non-microbial effects on pH and D.O.

Analytical methods to determine maximum utilization rates of ammonia, nitrate and oxygen are disclosed in the article "Characterization of Functional Microorganism Groups and Substrate in Activity Sludge and Wastewater by AUR, NUR and OUR," *Wat. Sci. Tech.*, Vol. 25, No. 6, pp. 43–57 (1992). However, there is no disclosure of a method of control which utilizes pHPR and BOCR together as control parameters for a microbiological process or any means for inhibiting non-microbial effects on pH and D.O.

A model of the nitrifying activated sludge process is used in the article "Effects of Oxygen Transport Limitation on Nitrification in the Activated Sludge Process," *Research Journal WPCF*, Vol. 63, No. 3, pp. 208–19 (1991) to investigate the effects of mass-transport resistance and heterotrophic/nitrifier competition on the apparent relationship between dissolved oxygen concentration and nitrification. However, there is no suggestion that pHPR and BOCR be used together as control parameters for a microbiological process or of any means for inhibiting non-microbial effects on pH and D.O.

There remains a need for a practical and convenient method, usable in virtually any microbiological process in a liquid medium, for monitoring transitions in microbial metabolic behavior and controlling a microbiological process according to those transitions.

OBJECTS OF THE INVENTION

It is an object of the present invention to provide a method for precisely monitoring transitions in metabolic behavior experienced by a microbial population upon depletion of exogenous, readily usable soluble organic and inorganic substrates below metabolically significant concentrations and/or levels.

It is another object of the invention to provide a method for controlling a process involving biological nutrient removal in fluids as a result of monitoring transitions in metabolic behavior experienced by a microbial population upon depletion of exogenous, readily usable soluble organic and inorganic substrates below metabolically significant concentrations and/or levels.

It is an object of the present invention to provide a method for precisely monitoring when the concentration of organic and/or ammonia substrate falls below a desired point during a microbiological process to maximize the efficiency of the microbiological process.

It is another object of the invention to provide a method for precisely monitoring when the concentration of organic and/or ammonia substrate falls below a desired point during a microbiological process which is unaffected by aeration of a fluid batch.

Other objects of the present invention will be apparent to those of ordinary skill in the art based on the following detailed description of preferred embodiments and the appended claims.

SUMMARY OF THE INVENTION

The method of the invention involves the isolation of a fluid sample from a fluid supply, such as wastewater in a purification process. BOCR and pHPR are calculated from D.O. and pH measurements taken from the fluid sample and analyzed to quickly determine when metabolically significant transition points occur. The analysis dictates what control steps are needed and when they should be implemented to maximize the efficiency of the process being monitored.

DETAILED DESCRIPTION OF THE INVENTION

Figure 1:
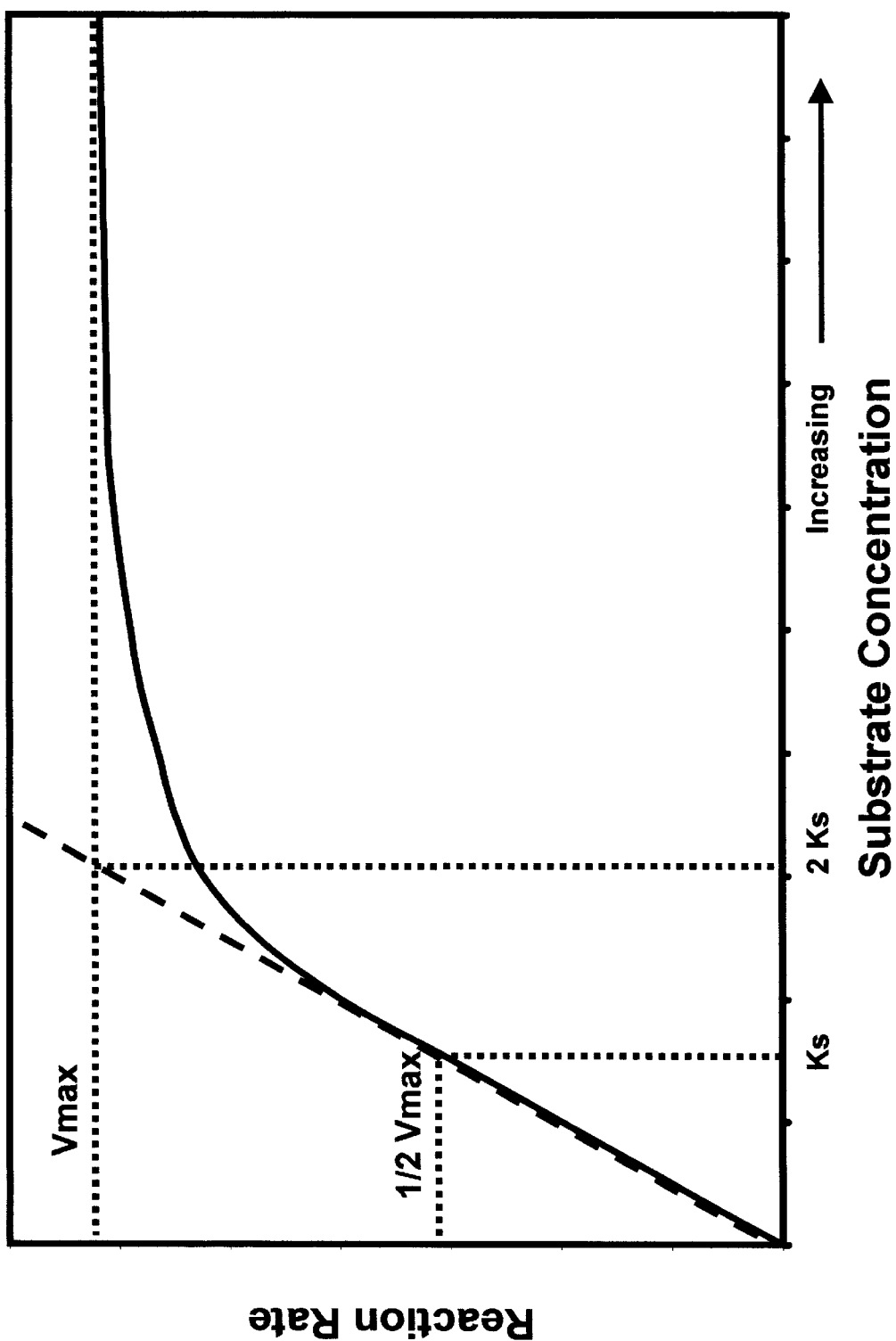
FIG. 1 is a graphic representation describing the Michaelis-Menten theory of reaction kinetics.

The mechanistic rate at which biochemical reactions proceed can be described in part by the Michaelis-Menten theory as illustrated in FIG. 1. This theory states that the rate of biochemical reaction is very low at very low substrate concentrations, but the rate increases as substrate concentration rises until a point is reached beyond which there are vanishingly small increases in the reaction rate no matter how much the substrate concentration rises. In other words, no matter how far the substrate concentration is raised beyond this point, the reaction rate will approach, but never reach a plateau. This plateau is the maximum reaction rate or $V_{max}$ and occurs at a substrate concentration equivalent to $2K_s$, where $K_s$ is the substrate concentration at which the metabolic reaction rate is one-half the maximum reaction rate ($V_{max}$).

It, therefore, follows that from a metabolic perspective, $2K_s$ is a significant substrate concentration. Microbial metabolism of a substrate proceeds above $2K_s$ at a maximum and nearly constant rate. The metabolic reaction rate can become variable and limited by substrate availability below $2K_s$. Consequently, changes in certain measurable parameters directly affected by and/or related to the rate of microbial metabolism of particular inorganic and organic substrates can be expected to change as the concentration of the particular substrate changes. Specifically, at a substrate concentration equal to or greater than $2K_s$, the dependent measurable parameter and/or the measured rate of change in this parameter over time would be expected to be relatively constant. As a substrate concentration decreases to below $2K_s$, the dependent measurable parameter and/or the measured rate of change in this parameter over time would be expected to differ markedly from the values measured when the substrate concentration was equal to or higher than $2K_s$.

For many biological reactions, it is desirable to determine the point at which certain substrates have been depleted below this metabolically significant $2K_s$ concentration. It is possible to detect changes in the pattern of metabolic behavior of a microbial culture by monitoring changes in certain dependent measurable parameters, as the concentrations of certain organic and inorganic substrates change.

For example, in many wastewater purification processes it is the object to reduce the concentrations of certain organic and inorganic substrates to very low levels. These substrates typically include those organic substrates collectively referred to and measured as BOD (biochemical oxygen demand) and/or COD (chemical oxygen demand) and inorganic ammonia ($NH_4^+$). Based on reactions (1) and (2), which are representative and typical of biochemical reactions involving the microbial assimilation of an inorganic substrate and an organic substrate, two relevant dependent parameters for monitoring and detecting changes in the availability of these organic and inorganic substrates would be oxygen utilization rate and rate of pH change, respectively. Assuming that the nitrification reaction and the BOD/COD reduction reaction were the two most predominant reactions, it would be expected that characteristic changes would be seen in both the oxygen utilization rate (BOCR) and rate of change in pH (PHPR) as BOD and ammonia are depleted below their respective $2K_s$ values.

A critical drawback of utilizing BOCR and pHPR as control parameters is that aeration of the fluid medium, as typically performed in the aerobic stage of a wastewater purification process to maintain an adequate supply of D.O. for biodegradation of contaminants, alters the pH and residual D.O. concentration of the medium unpredictably. Consequently, the relationship between parameters derived from those measurements (i.e., BOCR and pHPR) and metabolic activity is frequently destroyed. Further, simply halting aeration of the fluid medium for repeated measurement intervals severely compromises the efficiency of wastewater purification processes.

Utilization of a biological activity detection device such as that disclosed in U.S. Pat. No. 5,466,604, incorporated herein by reference, enables in situ isolation of wastewater samples from the main body of the wastewater under treatment. Isolation of a portion of the fluid prevents wastewater aeration or other non-microbial factors from affecting pH and D.O. unpredictably, thereby protecting the accuracy of BOCR and pHPR. Of course, other apparatus may be used in accordance with this invention. Also, the term "in situ" is used herein to describe any real-time fluid sample isolation process, irrespective of whether the sample remains in the main body of fluid, e.g. wastewater. In other words, apparatus may be used that physically removes the sample(s) from the fluid main body so long as measurements may be made substantially in "real-time" and/or "on-line."

Figure 2:
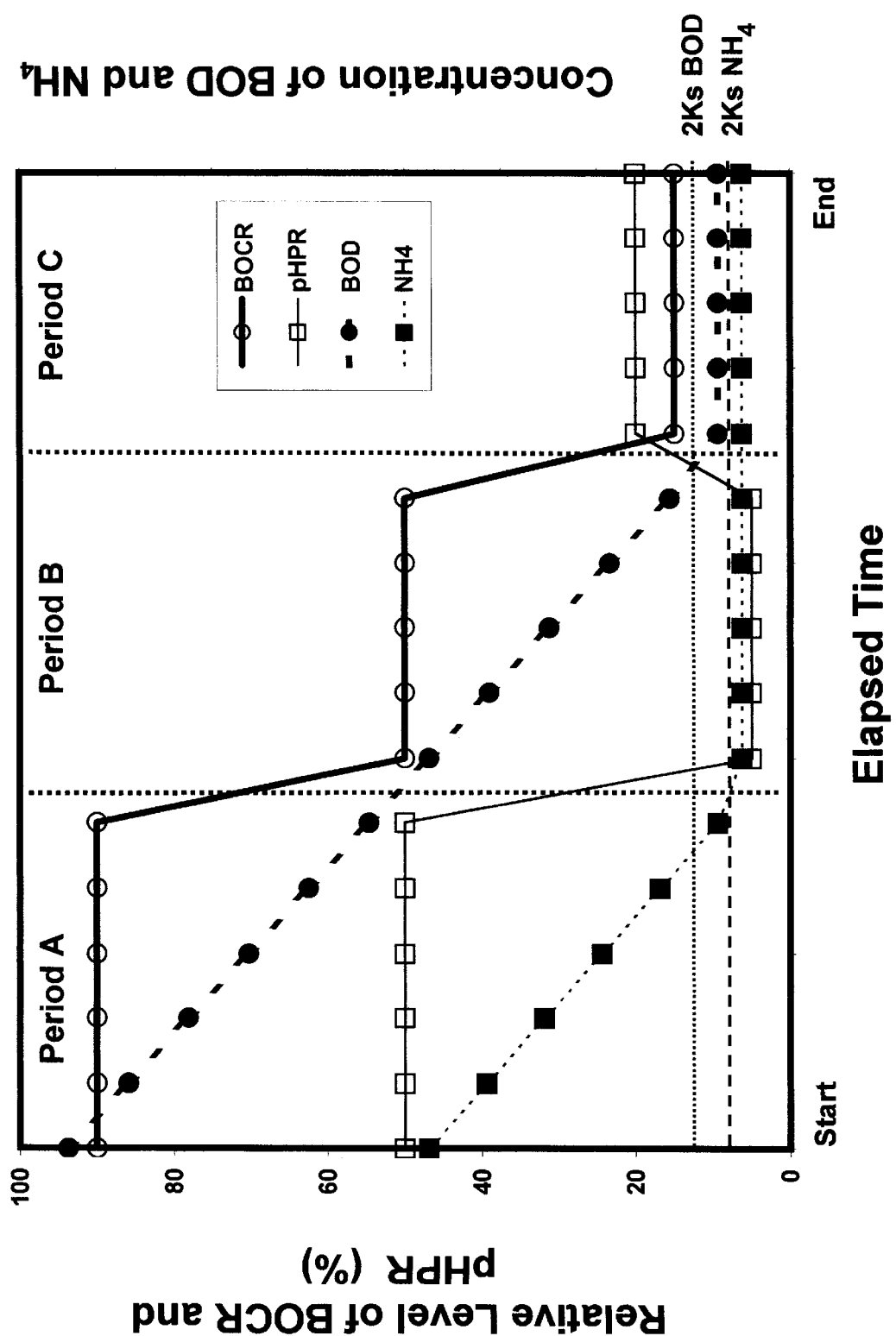
FIG. 2 is a graph depicting theoretical responses of oxygen utilization rate (BOCR) and rate of change in pH (PHPR) of a mixed liquor sample as concentrations of ammonia ($NH_4^+$) and organic carbonaceous material, collectively referred to as BOD (biochemical oxygen demand), change over time in a microbiological process.
Figure 3:
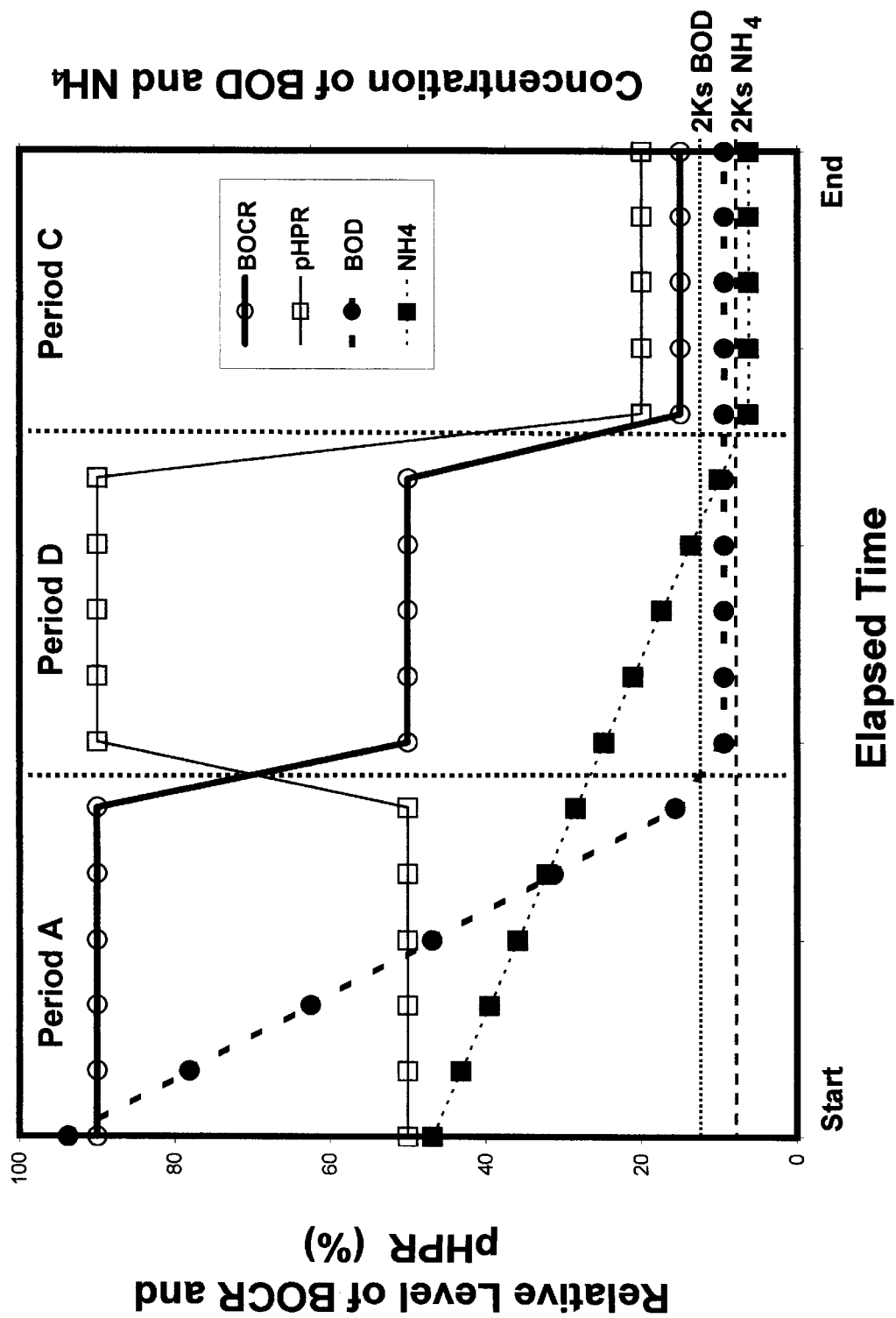
FIG. 3 is a graph depicting theoretical responses of oxygen utilization (BOCR) and rate of change in pH (PHPR) of a mixed liquor sample as the concentrations of ammonia ($NH_4^+$) and organic carbonaceous material, collectively referred to as BOD (biochemical oxygen demand), change over time in a microbiological process.

Theoretical responses of BOCR and pHPR to concentration changes in BOD and ammonia ($NH_4^+$) are depicted in FIGS. 2 and 3 and explained below. The Figures graphically represent responses from a single sample of mixed liquor (i.e., wastewater and microbes for biological nutrient removal (BNR) isolated from the main body of wastewater. The isolated sample is alternatively aerated and not aerated. Aeration begins and continues until a level of dissolved oxygen has been reached that is in excess of metabolic requirements. Once this level is reached, the aeration stops and only begins once the level of dissolved oxygen within the sample reaches twenty percent of the saturation level or less. During the periods where aeration is not conducted, both the oxygen utilization rate (BOCR) and rate of change in pH (pHPR) is evaluated and calculated as follows:

$$BOCR=(\Delta D.O.)/(\Delta t) \quad (6)$$

wherein $\Delta D.O.$ is equivalent to the change in saturation level of dissolved oxygen, expressed as percent saturation, measured over a time period $\Delta t$; and $$pHPR=(\Delta pH)/(\Delta t) \quad (7)$$

wherein $\Delta pH$ is equivalent to the change observed in pH over a time period $\Delta t$.

As shown in Period A of FIGS. 2 and 3, when both the concentrations of ammonia ($NH_4^+$) and BOD are above their respective $2K_s$ values, pHPR is constant since the nitrification reaction rate is constant, and BOCR is constant and at its highest relative level, since both the oxygen consuming reactions of nitrification (i.e., reaction 2) and BOD utilization (e.g., reaction 1) proceed at their maximum rates. This BOCR/pHPR pattern, as well as those described below, is expected assuming that 1) the nitrification and BOD utilizing reactions are the predominant reactions ongoing within the biological sample, 2) the production and activity of hydrogen ions are related to the rate of the nitrification reaction, and 3) the reactions are not limited by the availability of oxygen.

Subsequently, continued metabolism depletes the available ammonia ($NH_4^+$) below its $2K_s$ value and, the rate of nitrification, hydrogen ion production and hydrogen ion activity falls from a maximum rate to a lower rate where ammonia concentration is a metabolically limiting factor. As shown in Period B of FIG. 2, the rate of change of measured pH (pHPR) drops significantly to a comparatively low level and the oxygen utilization rate (BOCR) drops to a comparatively lower level to reflect the decreased demand and use of oxygen caused by the significantly lower nitrification reaction rate. The transition from an ammonia concentration above the $2K_s$ value to below the $2K_s$ value is depicted in the transition between periods A and B in FIG. 2.

Period C of FIGS. 2 and 3 shows that where the concentration of available ammonia ($NH_4^+$) is below its $2K_s$ value and upon depletion of BOD below its $2K_s$ value, the rate of change in pH (PHPR) increases very slightly to reflect the change in net metabolic behavior of the mixed biological population and the oxygen utilization rate (BOCR) drops to its lowest rate to reflect the very low oxygen utilization by BOD consuming and nitrification reactions. This transition is depicted between Periods B and C in FIG. 2.

Period D of FIG. 3 shows that where the concentration of BOD is below its $2K_s$ value, but the concentration of ammonia ($NH_4^+$) is above its $2K_s$ value, the rate of change in pH (PHPR) increases to its highest level reflecting a high rate of nitrification and the oxygen utilization rate (BOCR) drops to a moderate level reflecting a net decrease in total oxygen utilization caused by the decreased level of BOD consuming reactions. The highest rate of pH change (PHPR) is seen under this condition because the buffering effects of the BOD consuming reactions are absent. Normally, production of carbon dioxide ($CO_2$) in the BOD consuming reactions affords some pH buffering capacity to the sample via the carbonic acid system shown in Reactions (3)–(5). Thus, in the absence of BOD consuming reactions and the resulting production of carbon dioxide ($CO_2$), the rate of change in measured pH (PHPR) is much greater than in the other conditions.

It is possible to determine pertinent information about the biological sample based on the example provided above, by monitoring and comparing trends and/or levels of BOCR and pHPR because they represent key measurable, dependent parameters of microbial metabolic activity. Specifically, this example illustrates how a determination can be made as to whether 1) both nitrification and BOD removal are occurring simultaneously at maximum rates, 2) nitrification is occurring while BOD has been reduced to levels below its $2K_s$ value, 3) BOD removal reactions are ongoing while ammonia has been reduced below its $2K_s$ value, and 4) both ammonia and BOD have both been reduced below their respective $2K_s$ values.

Direct and continuous comparison of the measured parameters BOCR and pHPR leads to several conclusions about the condition of the wastewater. If a mixed liquor sample is continuously monitored and a large increase in pHPR occurs simultaneously with a decrease in BOCR, this indicates that BOD has been depleted below its respective $2K_s$ value while ammonia is still plentiful. If a mixed liquor sample is continuously monitored and BOCR decreases to a moderate level while pHPR decreases to a near zero level, it indicates that ammonia has been depleted below its respective $2K_s$ value while BOD is still plentiful. If a mixed liquor sample is continuously monitored and BOCR decreases to a low level while pHPR decreases to a low level, it indicates that both ammonia and BOD have been depleted below their respective $2K_s$ values. This condition is also indicated by a decrease in BOCR to a low level and slight increase in pHPR from a near zero level to a slightly higher, but low, level.

Table I summarizes these patterns and illustrates how comparison of the relative values and patterns of the measured parameters of oxygen utilization rate (BOCR) and rate of change in pH (pHPR) yields the pertinent information described above in conjunction with FIGS. 2 and 3.

TABLE I

| PERIOD | CONCENTRATION OF BOD | CONCENTRATION OF $ND_4^+$ | MEASURED PARAMETER | RELATIVE VALUE OF MEASURED PARAMETER |
|---|---|---|---|---|
| A | $>2K_s$ | $>2K_s$ | BOCR | HIGH |
|   |         |         | pHPR | MODERATE |
| B | $>2K_s$ | $<2K_s$ | BOCR | MODERATE |
|   |         |         | pHPR | NEAR ZERO |
| C | $<2K_s$ | $<2K_s$ | BOCR | LOW |
|   |         |         | pHPR | LOW |
| D | $<2K_s$ | $>2K_s$ | BOCR | MODERATE |
|   |         |         | pHPR | HIGH |

It is another practical benefit of this method that the pH and D.O. measuring devices need not be constantly recalibrated to provide pH and D.O. readings which reflect the actual pH and D.O. of the sample since only changes in pH and D.O. are important and not the true values of pH and D.O. of the sample.

A biological activity detection device embodying a preferred apparatus for practicing the invention will now be described. It is understood that any real-time sample isolation and monitoring apparatus can be used to practice the invention, and the following illustrative description is not intended to limit the scope of the appended claims.

Figure 4:
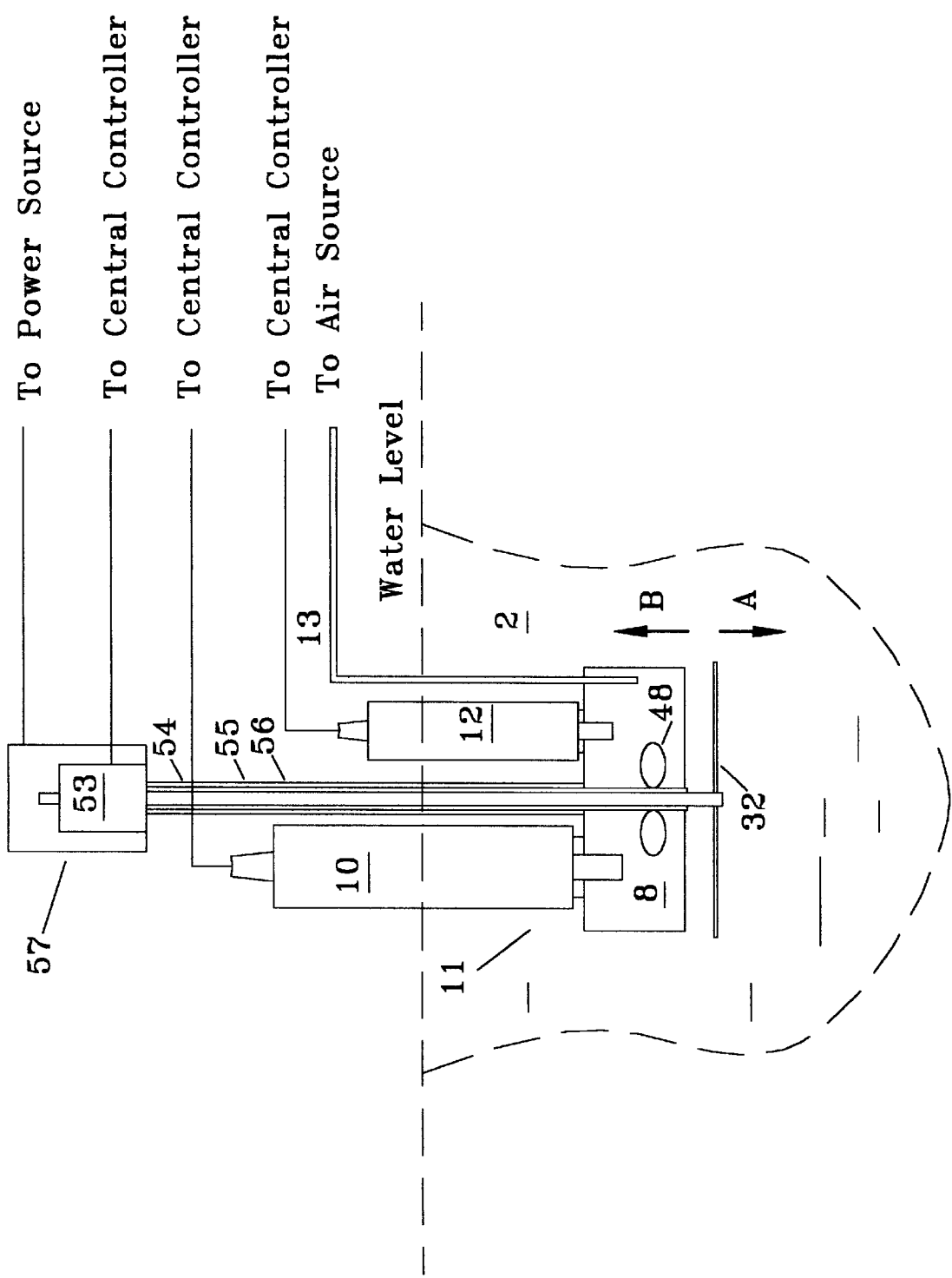
FIG. 4 shows a schematic front elevational view of one embodiment of apparatus which may be used to separate and monitor a fluid sample from a fluid supply in a bioreactor tank in accordance with the invention.

FIG. 4 shows an example of a preferred apparatus used to isolate a wastewater sample. The apparatus 11, immersed in wastewater batch 2 (only a portion of which is depicted), includes a detection chamber 8 having a movable cover 32. Movable cover 32 is pushed in the direction of arrow "A" by inner shaft 56 driven by an Acme shaft 57 connected to motor 53. At the open position, rotation of propeller 48 forces an exchange of wastewater between the inside and outside of detection chamber 8 and detection chamber 8 is filled with a fresh sample of wastewater. After a given period of time, e.g. 30 seconds, motor 53 is programmed to reverse its rotation direction, movable cover 32 is pulled in the direction of arrow "B" until detection chamber 8 is fully closed or sealed. The movable cover 32 and propeller 48 are driven by the same reversible low RPM motor 53 which coaxially connects inner shaft 56 and outer shaft 55. The coaxial assembly is shielded by stainless steel pipe 54.

The D.O. concentration is detected by D.O. probe 10 after filling detection chamber 8 with a fresh sample of wastewater and, if D.O. is less than a desired level of saturation, air and/or $O_2$ is pumped into detection chamber 8 through aeration tube 13 until that desired D.O. concentration is attained. The desired D.O. concentration is one that ensures that oxygen will not become a limiting factor for the aerobic metabolic reactions during the measurement interval described below. Similarly, pH probe 12 detects changes in pH. Additionally, propeller 48 may be periodically rotated to maintain the sample in a well-mixed condition.

Aeration in the apparatus 11 is interrupted for the measurement interval after the minimum initial D.O. concentration is attained. During this period, residual D.O. concentration and pH, both unaffected by aeration of the wastewater batch at large, are monitored through the probes. The pH and residual D.O. signals from the respective probes 12 and 10 are sent to controllers which convert changes in D.O. over time to BOCR and changes in pH over time to pHPR by numerical differentiation according to the equations (6) and (7) described above.

EXAMPLE

A mixed liquor sample recovered from the aerobic basin of an advanced biological wastewater treatment plant located in Oaks, Pa., was isolated in a vessel equipped with devices to measure sample pH and dissolved oxygen saturation levels, as well as devices to aerate and maintain the sample in a well mixed condition. The data from the devices measuring sample pH and dissolved oxygen saturation levels was recorded and analyzed by a computer to calculate the oxygen utilization rate (BOCR) and the rate of change in pH (pHPR). In the vessel the sample was exposed to fixed, alternating periods of aerated and non-aerated conditions. Aeration began and continued until a level of dissolved oxygen was reached that was at least eighty percent of the saturation level. Once this level was reached, aeration was stopped and only began once the level of dissolved oxygen within the sample fell to twenty percent of the saturation level. Concentrations of soluble ammonia ($NH_4^+$) and soluble carbonaceous organic substrates were measured and reported as COD (chemical oxygen demand). During the periods of non-aeration, examples of which are marked off with arrows on FIGS. 5 and 6, both the oxygen utilization rate (BOCR) and rate of change in pH (pHPR) was evaluated and calculated by numerical differentiation according to equations (6) and (7) described above.

Figure 5:
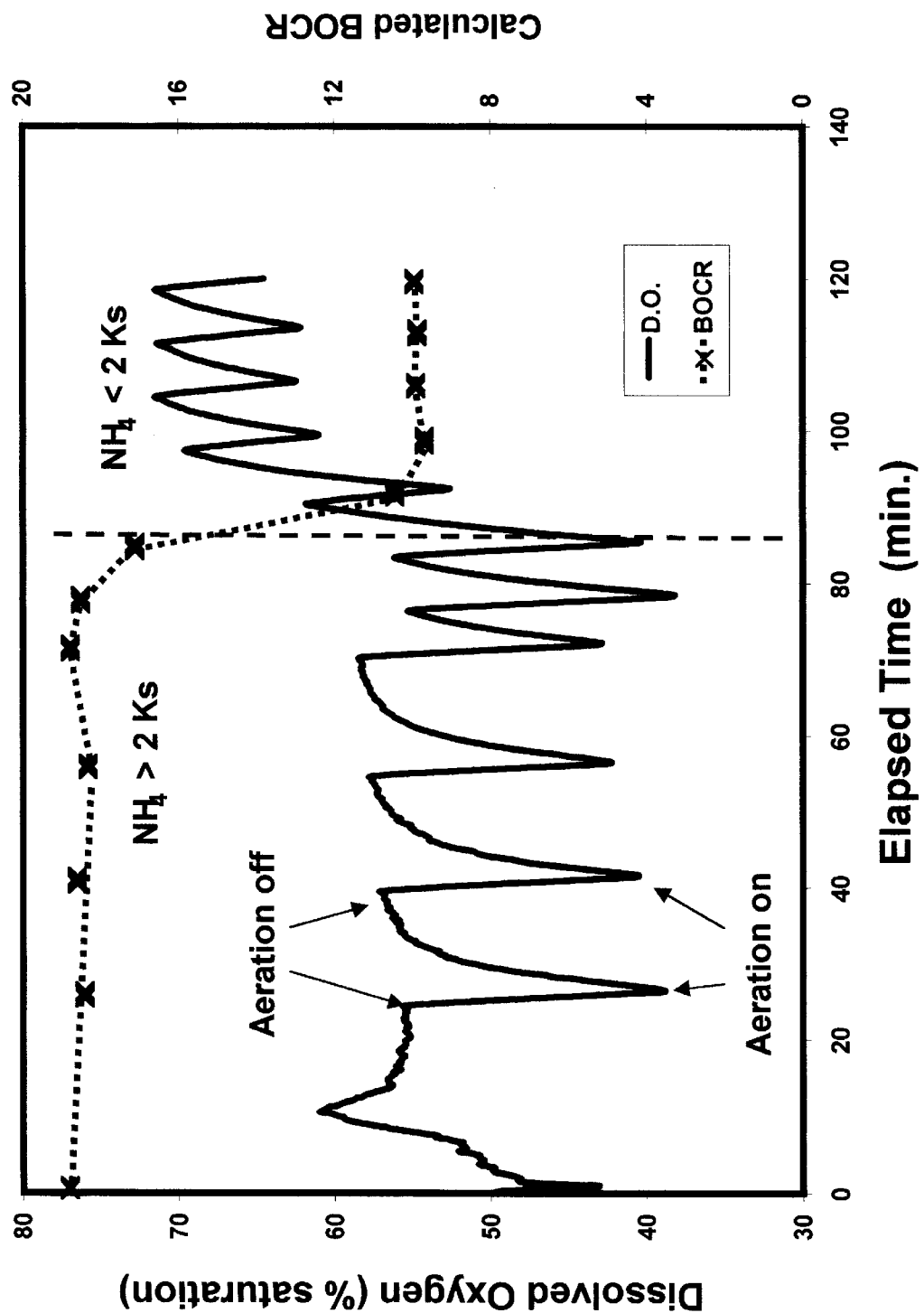
FIG. 5 graphically illustrates the relationship between the rate of oxygen change between the cessation and onset of aeration and BOCR expressed as % change in oxygen saturation per minute.

FIG. 5 shows dissolved oxygen saturation and BOCR during a period of the test where the measured COD concentration was consistently greater than 150 mg COD/L, which was well above the $2K_s$ value for COD, but where the ammonia concentration varied from a concentration above the $2K_s$ value to a concentration below the $2K_s$ value. FIG. 5 reveals the relationship between the raw dissolved oxygen data, that is the rate of oxygen change between the cessation and onset of aeration as indicated, and BOCR. FIG. 5 also illustrates the transition in the level of BOCR from a high to a moderate level during the metabolically significant transition when ammonia concentration dropped below its $2K_s$ value. BOCR is expressed as % change in oxygen saturation per minute.

Figure 6:
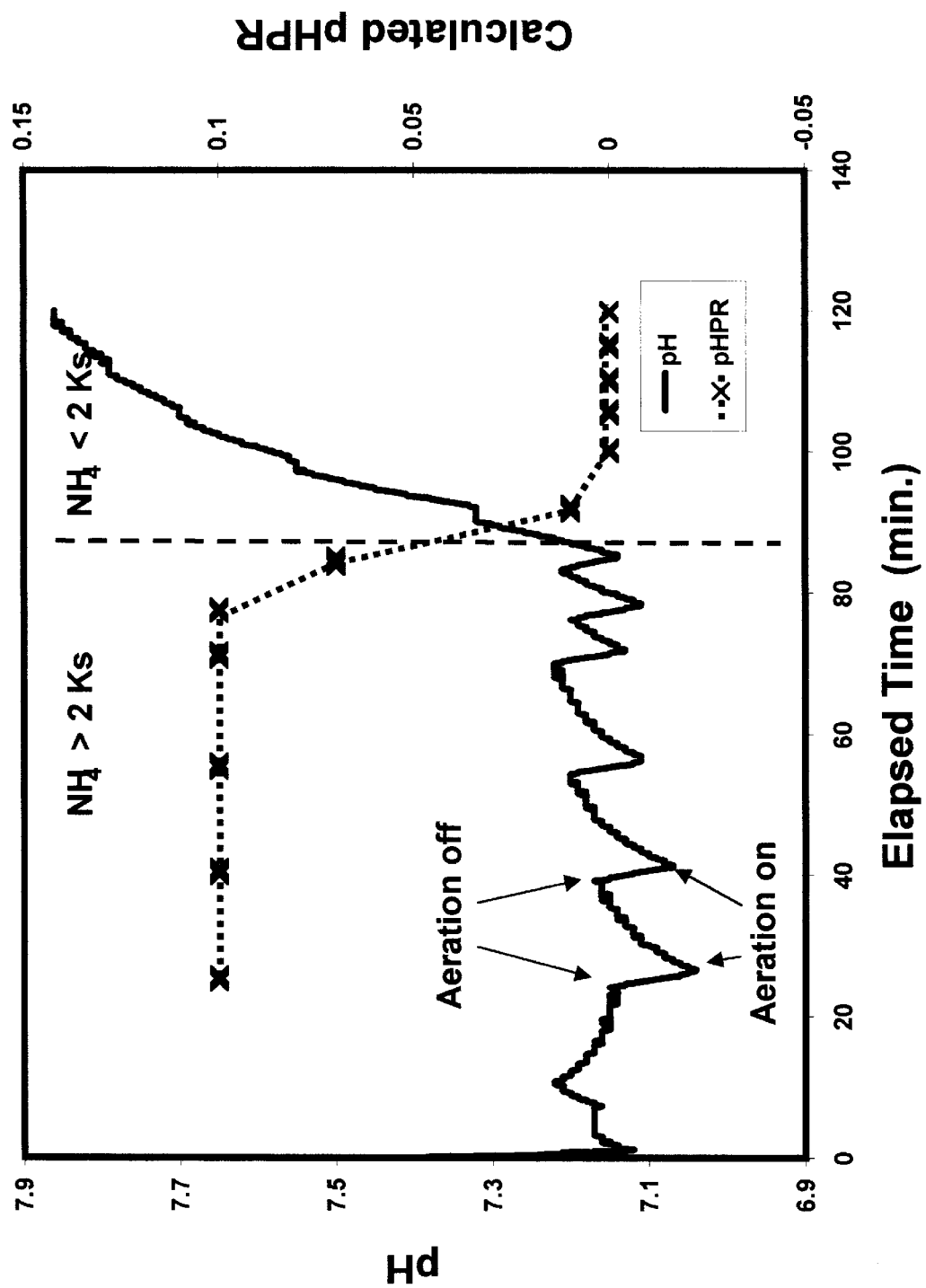
FIG. 6 graphically illustrates the relationship between the pH change between the cessation and onset of aeration and pHPR expressed as change in pH per minute as ammonia concentration changes.

FIG. 6 shows the sample pH and pHPR for the same period as depicted in FIG. 5. During this period the measured COD concentration was consistently greater than 150 mg COD/L, which was well above the $2K_s$ value for COD, but the ammonia concentration varied from above its $2K_s$ value to below the $2K_s$ value. FIG. 6 illustrates the relationship between the raw pH data, i.e, the pH change between the cessation and onset of aeration as indicated, and pHPR. FIG. 6 also illustrates the transition in pHPR from a moderate to a near zero level during the metabolically significant transition when the ammonia concentration dropped below its $2K_s$ value. pHPR is expressed as change in pH per minute.

Figure 7:
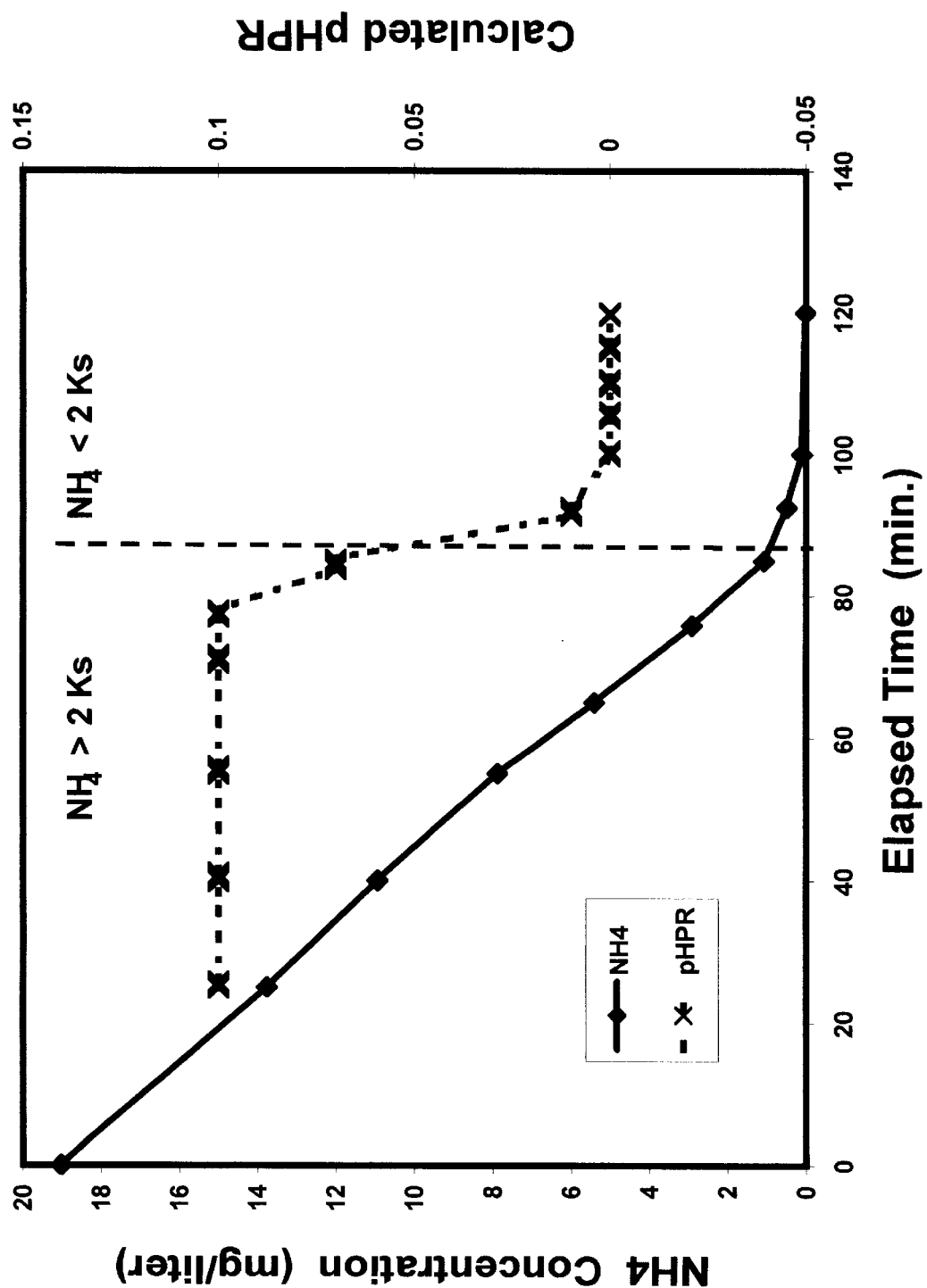
FIG. 7 graphically shows the relationship between pHPR expressed as change in pH per minute and ammonia concentration where COD is not a metabolically limiting factor.

FIG. 7 shows the changes in measured ammonia levels and calculated pHPR for the same period as depicted in FIG. 6. FIG. 7 illustrates the transition in pHPR from a moderate to a near zero level during the ammonia concentration transition from about $2K_s$ to below $2K_s$. pHPR is expressed as change in pH per minute.

Figure 8:
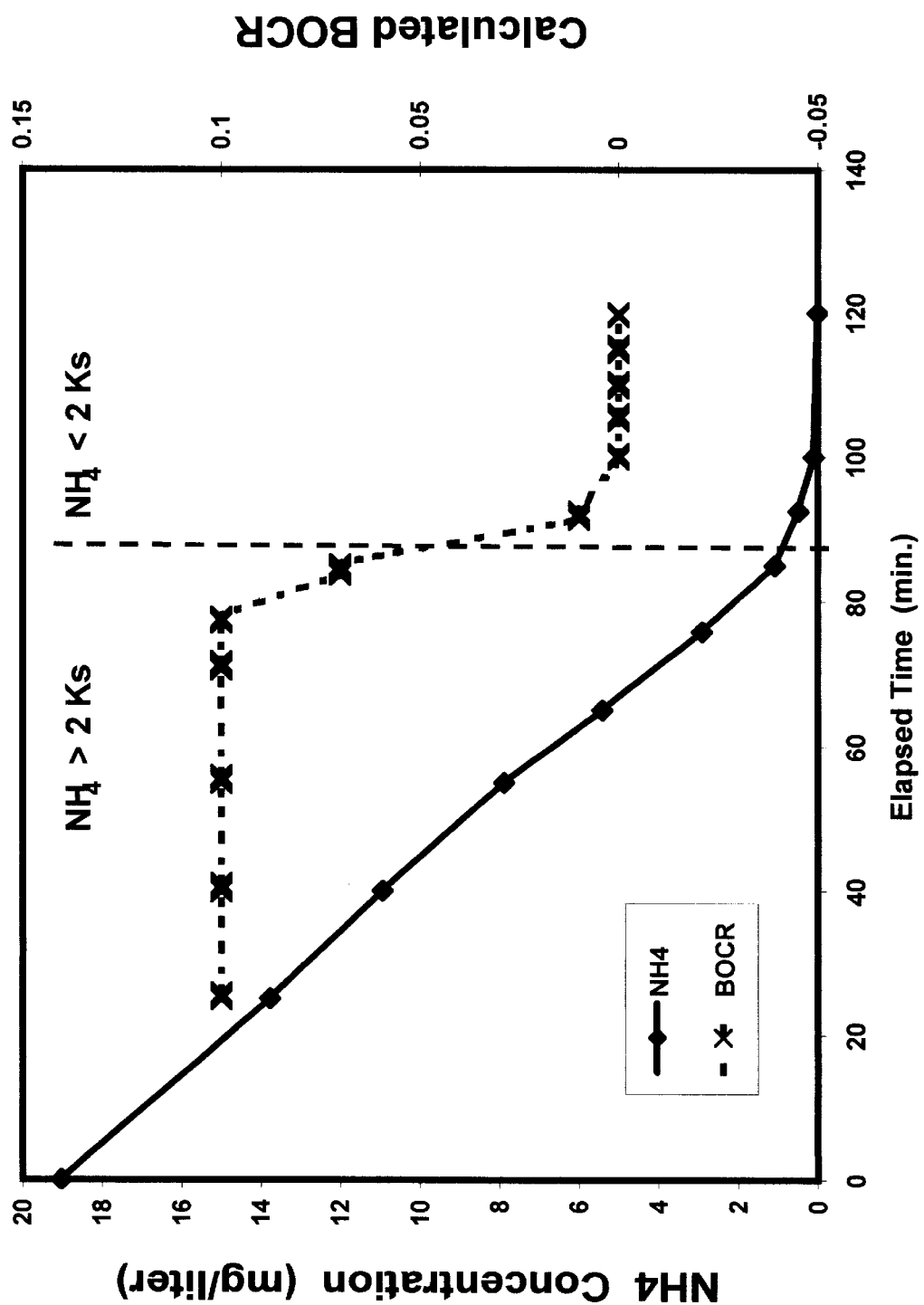
FIG. 8 graphically shows the relationship between BOCR expressed as % change in oxygen saturation per minute and ammonia concentration where COD is not a metabolically limiting factor.

FIG. 8 shows the changes in measured ammonia levels and calculated BOCR for the same period as depicted in FIG. 5. FIG. 8 illustrates the transition in BOCR from a high to a moderate level during the ammonia concentration transition from above $2K_s$ to below $2K_s$. BOCR is expressed as % change in oxygen saturation per minute.

Figure 9:
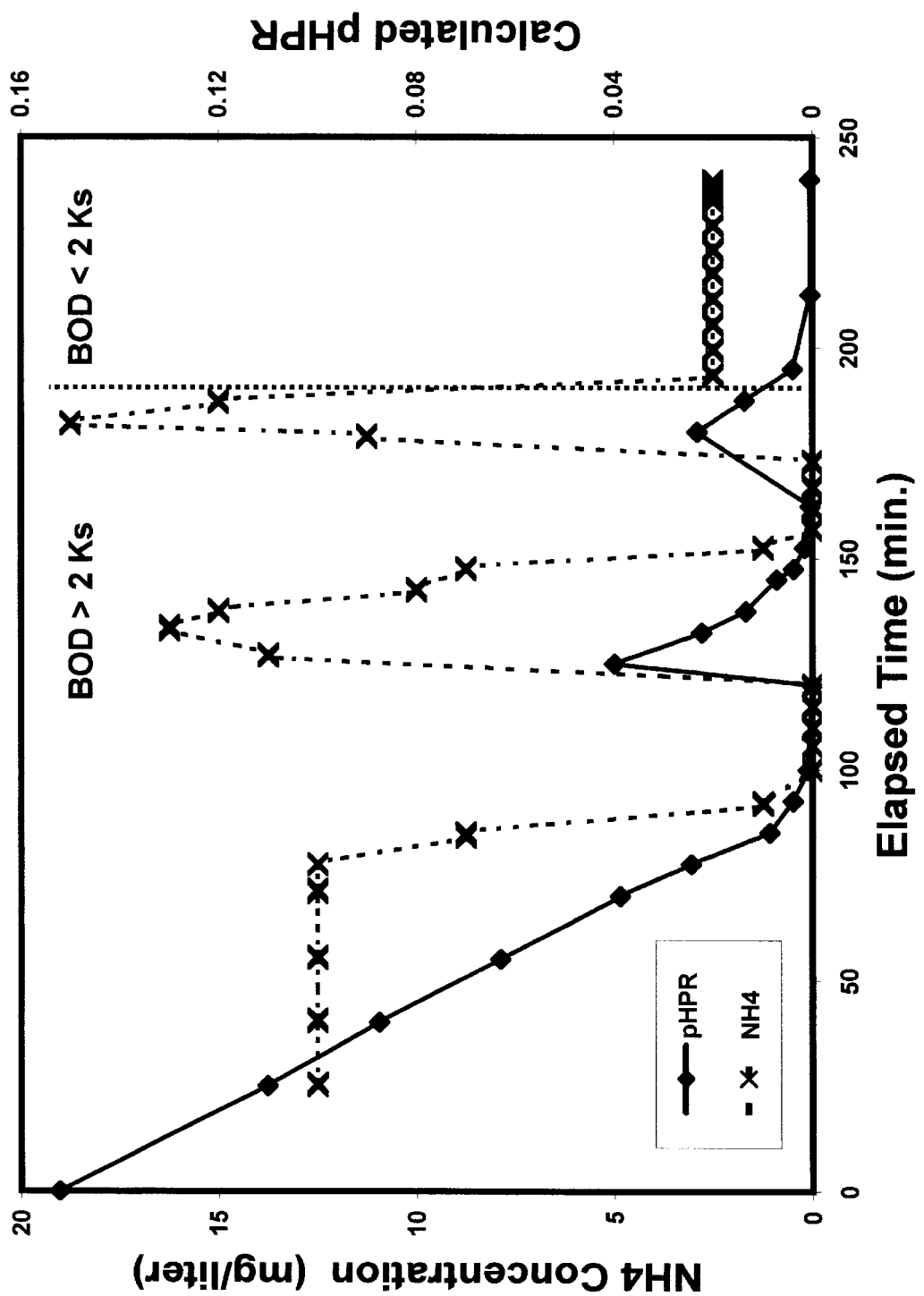
FIG. 9 shows the response of pHPR expressed as change in pH per minute under various conditions of ammonia and COD availability.

FIG. 9 graphically depicts the consistency of the response of pHPR to ammonia concentrations. This was accomplished by the addition of an ammonia solution to the mixed liquor sample at points where the ammonia contained within the sample was depleted, i.e., at T=120 and T=170 minutes. From the period between T=0 and T=195 minutes, COD concentration was well above its $2K_s$ value. After T=195 minutes, COD concentration dropped below its $2K_s$ value. At about T=90 minutes, a significant transition can be observed in pHPR as ammonia concentration is depleted below its $2K_s$ value.

Subsequent additions of ammonia were made at T=120 and T=170 minutes when pHPR was at a near zero level. FIG. 9 shows that pHPR jumped from the near zero level immediately before each subsequent addition to a comparably moderate level like that observed between T=0 and T=90 minutes. After the subsequent ammonia additions, pHPR returned to a near zero or low level upon depletion of ammonia below its $2K_s$ value. COD was plentiful and ammonia depletion resulted in a pHPR decrease to a near zero level in the case of the first ammonia addition at T=120 minutes. Ammonia depletion occurred at a time when COD concentration was also just depleted to below its $2K_s$ value in the second case of ammonia addition at T=170 minutes. Consequently, the pHPR decreases to a low, but not zero, level as shown in Period C of FIGS. 2 and 3.

Figure 10:
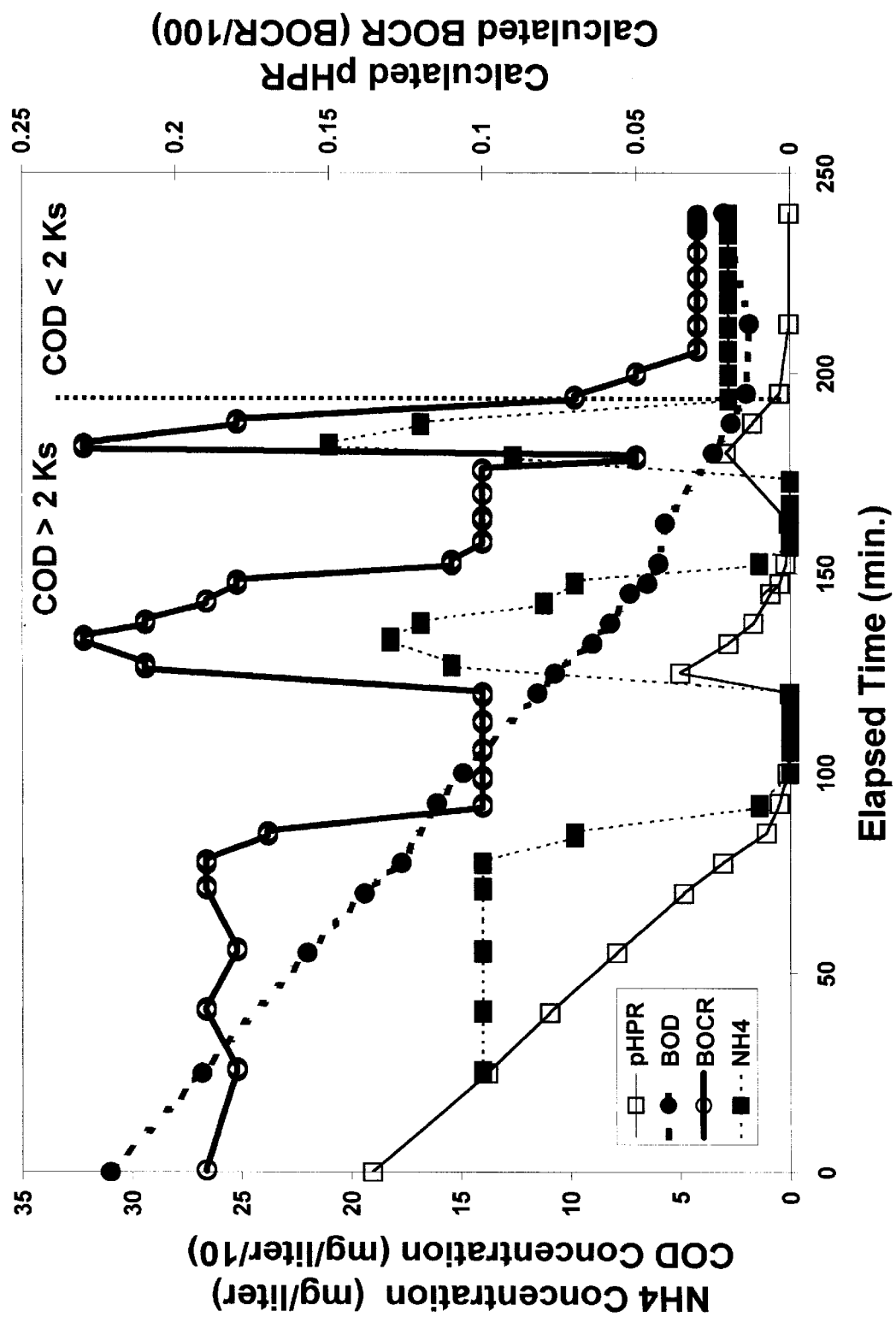
FIG. 10 shows the relationships between pHPR expressed as change in pH per minute, BOCR expressed as % change in oxygen saturation per minute, ammonia concentration and COD under various conditions of ammonia and COD availability.

FIG. 10 provides a more complete picture of the data shown in FIG. 9 and includes calculated pHPR, calculated BOCR, ammonia and COD concentrations. FIG. 10 best illustrates the transitions in pHPR and BOCR between the different relative levels as significant metabolic events occur.

It is possible to quickly and accurately ascertain the moment when the concentration of organic substrates and/or inorganic substrates fall below their respective $2K_s$ levels as evidenced by this Example, by monitoring relative levels of BOCR and pHPR, in accordance with the invention. Detecting the depletion of a particular substrate below its respective and metabolically significant $2K_s$ concentration value frequently signals a significant change in the condition of a microbial population or its environment, or a change in the metabolic pattern and/or behavior of a sample containing active microbes.

Various control steps may then be taken in response depending on the particular process. For example, the depletion of a particular substrate in a microbial population might signal a change in metabolism whereby the production of a desirable secondary metabolite may ensue, thus indicating that the process should proceed to a separation, collection and/or purification phase. Similarly, in biological processes where it is the object to maintain a particular step-feeding protocol of substrate to a microbial population, the capability to detect the depletion of this substrate below its $2K_s$ concentration and/or when substrate addition increase the substrate concentration above $2K_s$ can be used to indicate that increased or decreased feeding of substrate is desirable.

The Example involved aerobic biological wastewater purification, where it is often the object to reduce through biological mechanisms particular inorganic and organic substrates such as the reduction of soluble ammonia and carbonaceous organics. Thus, various control steps may be taken in response to the depletion of one or more of these substrates below its $2K_s$ concentration, as a concentration of $2K_s$ is often below the low concentration level targeted for many substrates. For example, if both organic and inorganic (ammonia) substrates are found to be below their respective $2K_s$ concentration values, the flow rate through the wastewater treatment process can be increased, thereby increasing the capacity of the treatment facility. If both organic and ammonia substrates are found to be above their respective $2K_s$ concentration values, the flow rate through the wastewater treatment process can be decreased. When ammonia substrate is below $2K_s$ but organic substrate is above $2K_s$, aeration of the batch can be decreased due to the reduced desire for nitrification. Finally, if the organic substrate is below $2K_s$ but ammonia substrate is above $2K_s$, aeration can be increased to create a more favorable condition for nitrification.

The invention provides a convenient method for quickly determining when the concentration of a particular substrate is below the metabolically significant $2K_s$ concentration so that control steps may be performed in a timely manner to improve the efficiency of the process. The invention may be applied to any kind of microbial process including, but not limited to, wastewater purification, pharmaceutical production, brewing or any other process involving pure or mixed populations of microorganisms.

Although this invention has been described with reference to specific forms of apparatus and method steps, it will be apparent to one of ordinary skill in the art that various equivalents may be substituted, the sequence of steps may be varied, and certain steps may be used independently of others. Further, various other control steps may be included, all without departing from the spirit and scope of the invention defined in the appended claims.

What is claimed is:

1. A method of monitoring a microbiological process in a fluid supply having a microbial population comprising:

a) isolating a fluid sample from said fluid supply;
   b) measuring the pH of said fluid sample at selected time intervals;
   c) determining a pH variation rate for said sample by calculating changes in pH, if any;
   d) measuring amounts of dissolved oxygen in said fluid sample at selected time intervals substantially synchronously with said measuring of pH; and
   e) determining a biological oxygen consumption rate for said sample by calculating changes in dissolved oxygen, if any.

2. The method defined in claim 1 wherein calculating changes in pH to determine said pH variation rate is performed according to the following formula:

$$pHPR=(\Delta pH)/(\Delta t)$$

wherein pHPR is said pH variation rate, $\Delta pH$ is a change in pH and $\Delta t$ is a change in time.

3. The method defined in claim 1 wherein said measuring of pH and dissolved oxygen is substantially continuous.

4. The method defined in claim 1 wherein calculating changes in D.O. to determine said biological oxygen consumption rate is performed according to the following formula:

$$BOCR = (\Delta D.O.)/(\Delta t)$$

wherein BOCR is said biological consumption rate, $\Delta D.O.$ is a change in dissolved oxygen and $\Delta t$ is a change in time.

5. The method defined in claim 1 further comprising repeating steps b) through e) at selected time intervals and comparing newly determined pH variation rate(s) and biological oxygen consumption rate(s) with previously determined pH variation rate(s) and biological oxygen consumption rate(s).

6. The method defined in claim 5 wherein comparing said newly determined pH variation rate(s) and biological oxygen consumption rate(s) with previously determined pH variation rate(s) and biological oxygen consumption rate(s) determines whether levels of organic and inorganic compounds in said fluid supply are greater or less than their respective $2K_s$ concentrations.

7. The method defined in claim 1, further comprising the step of performing a control step in response to changes in said pH variation rate(s) and/or said biological oxygen control rate(s), if any.

8. The method according to claim 7, wherein said fluid supply is aerated and has a fluid supply process flow, and wherein said control step is at least one treatment selected from the group consisting of increasing aeration of said fluid supply, decreasing aeration of said fluid supply, increasing said fluid supply process flow and decreasing said fluid supply process flow.

9. The method according to claim 7, wherein a feeding protocol of substrate additions is maintained for said microbial population, and wherein said control step comprises varying said substrate additions.

10. The method according to claim 7, wherein said microbiological process produces a desirable metabolite, and wherein said control step is at least one step selected from the group consisting of separation of said metabolite from said fluid supply, collection of said metabolite and purification of said metabolite.

11. The method defined in claim 1 wherein said step of isolating said fluid sample is performed in situ.

12. The method according to claim 1, wherein before said steps of measuring the pH and amounts of dissolved oxygen the fluid sample contains a desired dissolved oxygen content.

13. The method according to claim 1, wherein said fluid sample is isolated in a fluid sample chamber, said fluid sample chamber including an aerator capable of dissolving oxygen in said fluid sample and a sample agitator.

14. The method of claim 13, further comprising the steps of aerating said fluid sample with said aerator until said fluid sample contains a desired level of saturation of dissolved oxygen before the steps of measuring the pH and amounts of dissolved oxygen of said fluid sample, and periodically agitating said sample with said agitator during the steps of measuring the pH and amounts of dissolved oxygen of said fluid sample.

15. The method defined in claim 1 applied to a microbiological process selected from the group consisting of wastewater purification, pharmaceutical production and brewing.

16. A method of monitoring a microbiological process in a fluid supply having a microbial population comprising:

a) isolating a fluid sample from said fluid supply;

b) measuring the pH of said fluid sample at selected time intervals;

c) analyzing changes in pH, if any, to determine a pH variation rate for said sample;

d) measuring amounts of dissolved oxygen in said fluid sample at selected time intervals substantially synchronously with said measuring of pH;

e) analyzing changes in dissolved oxygen, if any, to determine a biological oxygen consumption rate for said sample; and f) repeating steps b) through e) at selected time intervals and comparing newly determined pH variation rate(s) and biological oxygen consumption rate(s) with previously determined pH variation rate(s) and biological oxygen consumption rate(s);

wherein step f) determines whether levels of organic and inorganic compounds in said fluid supply are greater or less than their respective $2K_s$ concentrations.

17. A method of monitoring and controlling a microbiological process in a fluid supply having a microbial population comprising:

a) isolating a fluid sample from said fluid supply;

b) measuring the pH of said fluid sample at selected time intervals;

c) analyzing changes in pH, if any, to determine a pH variation rate for said sample according to the following formula:

$$pHPR = (\Delta pH)/(\Delta t)$$

wherein pHPR is said pH variation rate, $\Delta pH$ is a change in pH and $\Delta t$ is a change in time;

d) measuring amounts of dissolved oxygen in said fluid sample at selected time intervals substantially synchronously with said measuring of pH;

e) analyzing changes in dissolved oxygen, if any, to determine a biological oxygen consumption rate for said sample according to the following formula:

$$BOCR = (\Delta D.O.)/(\Delta t)$$

wherein BOCR is said biological consumption rate, $\Delta D.O.$ is a change in dissolved oxygen and $\Delta t$ is a change in time;

f) repeating steps b) through e) at selected time intervals in comparing newly determined pH variation rate(s) and biological oxygen consumption rate(s) with previously determined pH variation rate(s) and biological oxygen consumption rate(s) to determine whether levels of organic and inorganic compounds in said fluid supply are greater or less than their respective $2K_s$ concentration; and g) performing a control step in response to determined levels of organic and inorganic compounds in said fluid supply based on their respective $2K_s$ concentrations.

18. The method of claim 1 wherein said fluid supply is a wastewater supply and said fluid sample is a wastewater sample.

19. The method of claim 16 wherein said fluid supply is a wastewater supply and said fluid sample is a wastewater sample.

20. The method of claim 17 wherein said fluid supply is a wastewater supply and said fluid sample is a wastewater sample.

* * * * *